US012102477B2

(12) United States Patent
Brinley Rajagopal et al.

(10) Patent No.: US 12,102,477 B2
(45) Date of Patent: *Oct. 1, 2024

(54) ULTRASOUND MEASUREMENT DEVICE

(71) Applicant: California Institute of Technology, Pasadena, CA (US)

(72) Inventors: Alaina Ann Brinley Rajagopal, Pasadena, CA (US); Aditya Rajagopal, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/128,998

(22) Filed: Mar. 30, 2023

(65) Prior Publication Data

US 2023/0240646 A1   Aug. 3, 2023

Related U.S. Application Data

(63) Continuation of application No. 16/547,544, filed on Aug. 21, 2019, now Pat. No. 11,660,066.

(Continued)

(51) Int. Cl.
*A61B 8/00* (2006.01)
*A61B 8/08* (2006.01)
(Continued)

(52) U.S. Cl.
CPC .............. *A61B 8/0891* (2013.01); *A61B 8/14* (2013.01); *A61B 8/40* (2013.01); *A61B 8/4236* (2013.01); *A61B 8/4472* (2013.01); *G01S 15/895* (2013.01)

(58) Field of Classification Search
CPC .. A61B 8/06; A61B 8/14; A61B 8/488; A61B 8/0891; A61B 8/40; A61B 8/4236;
(Continued)

(56) References Cited

U.S. PATENT DOCUMENTS 5,070,734 A   12/1991   Kawabuchi et al.
5,800,359 A   9/1998   Medero et al.
(Continued)

FOREIGN PATENT DOCUMENTS

CN   1980687 A   6/2007
CN   101150989 A   3/2008
(Continued)

OTHER PUBLICATIONS

International Preliminary Report on Patentability for Application No. PCT/US2019/047593, dated Mar. 4, 2021.
(Continued)

*Primary Examiner* — Boniface N Nganga
(74) *Attorney, Agent, or Firm* — Sheppard Mullin Richter & Hampton LLP

(57) ABSTRACT

An ultrasound measurement device includes: a processing device and multiple ultrasound sensors that capture tomographic information of a physiological structure. The ultrasound sensors include a first ultrasound sensor including a first transducer having a first frequency response with a first resonant frequency, and a second ultrasound sensor including a second transducer having a second frequency response with a second resonant frequency different from the first resonant frequency. The first frequency response partially overlaps with the second frequency response. The second transducer transmits an ultrasound signal that is reflected by the physiological structure to create a reflected ultrasound signal, the first transducer generates a first received signal from the reflected ultrasound signal, the second transducer generates a second received signal from the reflected ultrasound signal, and the processing device normalizes the first received signal with the second received signal or the second received signal with the first received signal.

20 Claims, 7 Drawing Sheets

Related U.S. Application Data

(60) Provisional application No. 62/720,405, filed on Aug. 21, 2018.

(51) Int. Cl.
*A61B 8/14* (2006.01)
*G01S 15/89* (2006.01)

(58) Field of Classification Search
CPC .. A61B 8/4472; G01S 15/895; G01S 15/8952
See application file for complete search history.

(56) References Cited

U.S. PATENT DOCUMENTS

| | | |
|---|---|---|
| 6,176,832 B1 | 1/2001 | Habu |
| 7,437,947 B1 | 10/2008 | Shen et al. |
| 8,657,755 B2 | 2/2014 | Parfenov et al. |
| 9,250,251 B2 | 2/2016 | Nicolaides et al. |
| 9,603,533 B2 | 3/2017 | Lading et al. |
| 11,103,211 B2 | 8/2021 | Liu et al. |
| 2004/0116813 A1 | 6/2004 | Selzer et al. |
| 2006/0079773 A1 | 4/2006 | Mourad et al. |
| 2011/0137173 A1 | 6/2011 | Lowe et al. |
| 2013/0303923 A1 | 11/2013 | Lerner et al. |
| 2014/0276062 A1 | 9/2014 | Kondoh |
| 2016/0345930 A1 | 12/2016 | Mizukami |
| 2017/0360397 A1 | 12/2017 | Rothberg |

FOREIGN PATENT DOCUMENTS

| | | |
|---|---|---|
| CN | 102481103 A | 5/2012 |
| CN | 103385703 A | 11/2013 |
| CN | 103648374 A | 3/2014 |
| CN | 104010566 A | 8/2014 |
| CN | 104749384 A | 7/2015 |
| CN | 105580049 A | 5/2016 |
| CN | 109414222 A | 3/2019 |
| WO | 02/43564 A2 | 6/2002 |
| WO | 2014/066859 A1 | 5/2014 |
| WO | 2014/155265 A1 | 10/2014 |

OTHER PUBLICATIONS

International Search Report and Written Opinion for Application No. PCT/US2019/047593, dated Nov. 12, 2019.

First Office Action and Search Report dated Dec. 13, 2023, issued in related Chinese Application No. 201980054869.5, with English machine translation (20 pages).

Yaqin Xiong et al., "Study on the Application of Color Doppler Ultrasound-Guided Aortic Balloon Occlusion in Pelvic and Sacrococcygeal Tumor Surgery", Journal of Sichuan University (Medical Science Edition), 43(5), May 31, 2012, pp. 715-719, with English language abstract.

Xiaojie Xie et al., "Abnormal Pregnancy", Chinese Medical Abstracts: Family Planning and Obstetrics and Gynecology, Third Issue, Mar. 31, 1999, pp. 144-158, with English machine translation.

Wufeng Huang et al., "Effect of Microbubble Cavitation on Microcirculation in Skeletal Muscles of Rats", Journal of Southern Medical University, 2006 (12), Dec. 31, 2006, pp. 1690-1693, with English language abstract.

Notification of the Decision to Grant dated May 17, 2024, issued in related Chinese Application No. 201980054869.5, with English machine translation (7 pages).

100
ULTRASOUND MEASUREMENT DEVICE

CROSS-REFERENCE TO RELATED APPLICATIONS

This application is a continuation of and claims priority to U.S. application Ser. No. 16/547,544 filed Aug. 21, 2019 and titled "A Wireless Multimodal Monitoring Device", which claims priority to U.S. Provisional Application No. 62/720,405 filed Aug. 21, 2018 and titled "A Wireless Multimodal Monitoring Device". All of the above applications are incorporated herein by reference in their entirety.

BACKGROUND

Acoustic and optical imaging are routinely utilized for medical diagnosis. For example, x-ray transmission photography is used to visualize bone fractures. Similarly, ultrasound is used to visualize cardiac function. These visualizations drive patient diagnosis by providing medical practitioners with critical information on patient physiology.

Both acoustic and optical imaging tools interrogate patient physiology with a plurality of monochromatic transducers. These devices record the reflected power and received phase of each individual transmission, and map these recordings onto a two-dimensional (2D) or three-dimensional (3D) image. These images are human-interpreted to infer features such as physiology.

SUMMARY

Systems and methods described herein are directed to an ultrasound monitoring device.

In one embodiment, an ultrasound measurement device comprises: a plurality of ultrasound sensors configured to capture tomographical information of a physiological structure, each of the plurality of ultrasound sensors comprising a transducer having a respective resonant frequency, wherein each of the transducers has a frequency response that partially overlaps with a frequency response of another one of the transducers; and a processing device to control and process measurements made by the plurality of ultrasound sensors. During capture of tomographical information of the physiological structure, each of the transducers may be configured to be actuated in a time-interleaved fashion to capture images of a surface of the physiological structure at a plurality of depths.

In some implementations, the ultrasound measurement device further comprises: a substrate, where the substrate comprises an adhesive surface for adhering to a patient's skin, where the plurality of ultrasound sensors are incorporated in the substrate. The substrate may comprise one or more alignment markers for aligning the device with an artery of the patient. After the substrate is aligned with the artery, the processing device may be configured to use the plurality of ultrasound sensors to compute a mean arterial pressure through the artery.

The processing device may be configured to use the plurality of ultrasound sensors to compute the mean arterial pressure through the artery by performing operations of: measuring a circumference of the artery using the plurality of ultrasound sensors; measuring a blood flow velocity using the plurality of ultrasound sensors; and computing the mean arterial pressure using the measured arterial circumference and blood flow velocity.

In some implementations, the circumference of the artery is measured with the plurality of ultrasound sensors using echo-mode ultrasonography. In some implementations, the blood velocity is measured with the plurality of ultrasound sensors using continuous-wave ultrasound.

In some implementations, the ultrasound measurement device further comprises: a wireless transmitter, wherein the wireless transmitter is configured to transmit the computed mean arterial pressure to a display system for display. In other implementations, the ultrasound measurement device comprises a display, wherein the display is configured to display the computed mean arterial pressure.

In some implementations, the processing device is configured to use the plurality of ultrasound sensors to iteratively recompute the mean arterial pressure through the artery to account for beat by beat variations in arterial pressure.

In some implementations, the ultrasound measurement device further comprises: a plurality of non-ultrasound sensors, wherein each of the plurality of non-ultrasound sensors are configured to make measurements that are correlated and normalized with ultrasound measurements made by the plurality of ultrasound sensors.

In one embodiment, a method comprises: aligning a substrate with a patient's artery, wherein the aligned substrate comprises an ultrasound measurement device, the ultrasound measurement device comprising a plurality of ultrasound sensors, each the plurality of ultrasound sensors comprising a transducer having a respective resonant frequency; adhering the aligned substrate to the patient; measuring a circumference of the artery using the plurality of ultrasound sensors of the adhered substrate; measuring a blood flow velocity using the plurality of ultrasound sensors of the adhered substrate; and computing a mean arterial pressure using the measured arterial circumference and blood flow velocity.

In some implementations, the circumference of the artery is measured with the plurality of ultrasound sensors using echo-mode ultrasonography. In some implementations, the blood velocity is measured with the plurality of ultrasound sensors using continuous-wave ultrasound. In some implementations, the patient's mean arterial pressure is computed by modeling the measured blood flow velocity as a Stokes flow velocity, and normalizing it by the measured circumference.

In some implementations, the method further comprises: using a wireless transmitter of the ultrasound measurement device to transmit the computed mean arterial pressure to a display system for display.

In some implementations, the method further comprises: iteratively computing the mean arterial pressure and transmitting the computed mean arterial pressure to the display system such that the display system dynamically updates a display of the mean arterial pressure.

In one embodiment, a system comprises: an adhesive substrate configured to be adhered to a patient's skin, the adhesive substrate comprising an ultrasound measurement device, the ultrasound measurement device, comprising: a plurality of ultrasound sensors configured to capture tomographical information of a physiological structure, each of the plurality of ultrasound sensors comprising a transducer having a respective resonant frequency, wherein each of the transducers has a frequency response that partially overlaps with a frequency response of another one of the transducers; and a processing device configured to use the plurality of ultrasound sensors to compute a mean arterial pressure through an artery of a patient after the adhesive substrate is adhered to the patient; and a wireless transmitter configured to transmit the computed mean arterial pressure to a display system for display. In some implementations of this embodiment, the system further comprises: the display system, wherein the display system is configured to display an interface including dynamic measurements of vitals of the patient, the measurements comprising the computed mean arterial pressure, wherein a background of the interface is configured to dynamically provide a visual indication of the normality or abnormality of the patient's vitals.

Other features and aspects of the disclosure will become apparent from the following detailed description, taken in conjunction with the accompanying drawings, which illustrate, by way of example, the features in accordance with various embodiments. The summary is not intended to limit the scope of the invention, which is defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

Figure 1:
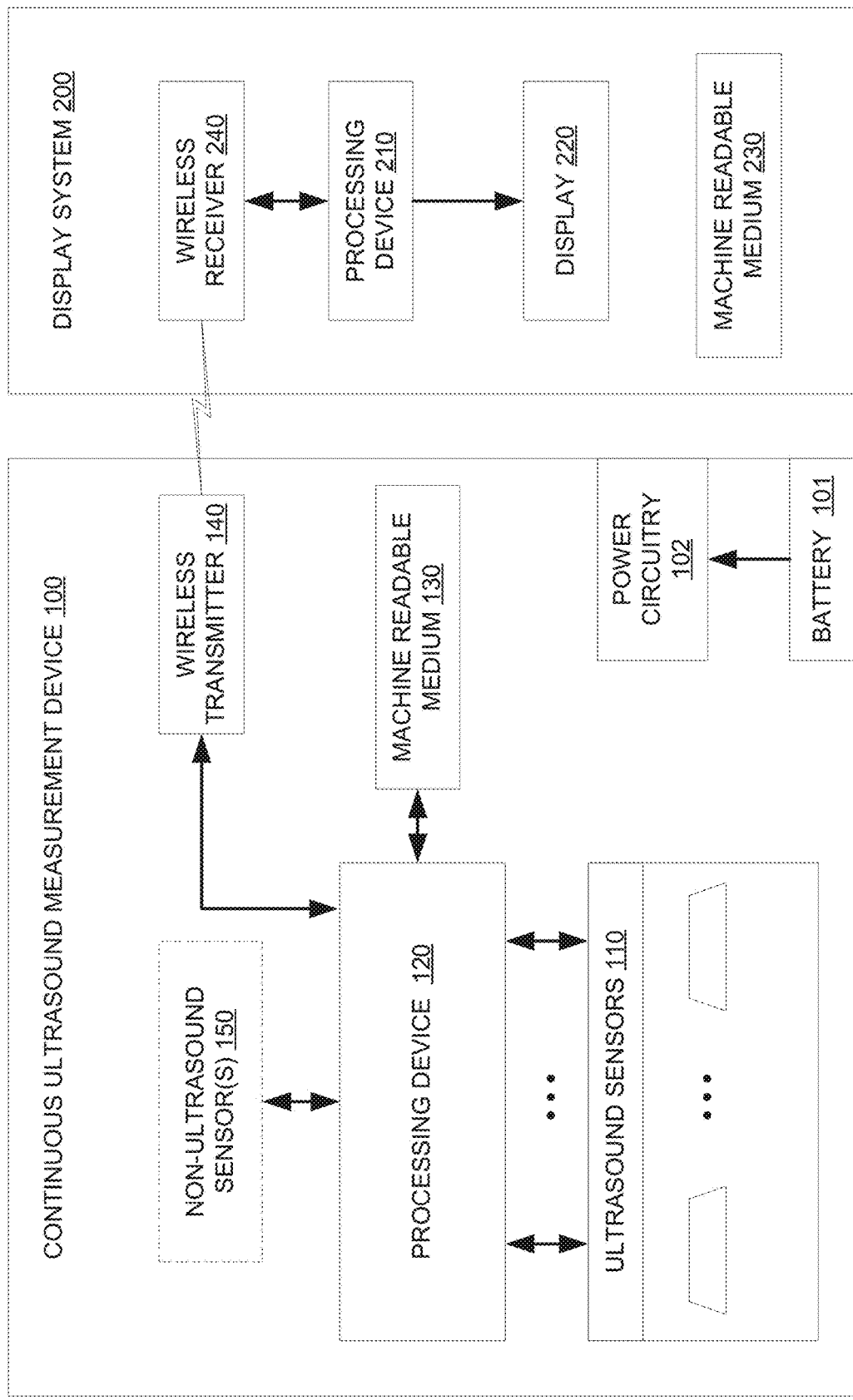
FIG. 1 is a block diagram illustrating some components of a continuous ultrasound measurement device, in accordance with implementations of the disclosure.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION

As used herein to refer to a transducer, the term "resonant frequency" generally refers to an operating frequency at which the transducer most efficiently converts electrical energy into mechanical energy. For example, in the context of a piezoelectric transducer, the term resonant frequency may refer to an operating frequency at which the piezoelectrical material most readily vibrates and converts electrical energy into mechanical energy most efficiently.

Unlike free space imaging, tissue imaging is plagued by poor optical and acoustic transmissivity as well as beam scattering. A number of strategies have been developed to mitigate for the low signals in the noisy tissue environment. For example, in ultrasound imaging, both the transmitter and receiver are resonance matched to maximize the receiver power and thus the signal strength. This may be used in echo mode ultrasonography, a technique for recording the reflection of ultrasound waves off the surface of objects, to significantly improve contrast and resolution of ultrasound images. Additionally, a phased array of multiple ultrasound transducers may be operated at a single frequency. By varying the timing at which each transducer is pulsed, an ultrasonic beam may be steered electronically through the tissue to increase the spatial component of the captured image (e.g., to capture a "slice" of tissue). However, the advantages of the aforementioned approaches (e.g., increase in signal strength and high spatial component) come at the cost of limited tomography. In particular, single wavelength ultrasound is critically limited in the depth of tissue it can measure.

To address the aforementioned deficiencies of present ultrasonography systems and methods, the technology disclosed herein is directed to a multi-wavelength ultrasound imaging device that collects information from a plurality of ultrasound sensors, where each sensor has an ultrasound transducer with a unique resonance frequency. By virtue of insonating physiology with multiple ultrasound sensors operating at distinct resonance frequencies, ultrasound emitted by the plurality of transducers may simultaneously penetrate various depths in a given cross-sectional area of physiology (e.g., tissue). In particular, ultrasound sensors having acoustic frequency responses may be actuated in a time interleaved fashion such that each sensor may be used to image a physiological surface at a unique depth. This may enable high resolution tomography without needing to increase the gain or the number of ultrasound imaging sensors. Furthermore, each sensor may be simultaneously actuated with a combination of other sensors to generate higher order harmonics which allow for sub-pixel feature resolution (i.e., super resolution imaging).

FIG. 1 is a block diagram illustrating some components of a continuous ultrasound measurement device 100, in accordance with implementations of the disclosure. As depicted, device 100 includes a plurality of ultrasound sensors 110, a processing device 120, a machine readable medium 130, a wireless transmitter 140, and, optionally, one or more non-ultrasound sensor(s) 150. The electrical components device 100 may be powered by a battery 101 that connects to power circuitry 102 for distributing power. The battery 101 may be rechargeable (e.g., via a USB port and/or an AC/DC converter). Although a battery 101 is shown in this example, it should be appreciated that any suitable battery or power supply technologies may be used to power the components of device 100. For example, lithium-ion batteries, cell batteries, piezo or vibration energy harvesters, photovoltaic cells, AC/DC sources, or other like devices can be used.

During operation, processing device 120 may collect information from the plurality ultrasound sensors 110 (individually referred to as "an ultrasound sensor 110") to collect imaging data of a subject (e.g., tissue of a subject). Each ultrasound sensor 110 includes a transducer configured to convert electricity to ultrasound and vice versa. For example, the transducer may be a piezoelectric transducer that oscillates and produces an ultrasonic pulse when an AC voltage is applied. Alternatively, the transducer may be a capacitive transducer that produces ultrasonic soundwaves using electrostatic fields between a conductive diaphragm and a backing plate. ultrasound soundwaves may be a produced at a frequency greater than or equal to about 20 kilohertz (KHz). In implementations, the transducers of ultrasound sensors 110 may produce ultrasound in a frequency anywhere between 2 megahertz (MHz) and 20 MHz. When a reflected ultrasound signal (i.e., an "echo") is received by the transducer, an electrical signal may be generated and used by ultrasound sensor 110 to determine a distance to the imaged subject.

Ultrasound that enters tissue may be transmitted, attenuated or reflected. While higher frequency ultrasound may provide for a higher resolution signal, it may provide poor depth penetration of imaged tissue. Conversely, while lower frequency ultrasound may provide for a lower resolution signal, it may provide better depth penetration of imaged tissue. To overcome these limitations of conventional ultrasound imaging systems, each ultrasound sensor 110 may have a transducer configured with a unique resonance frequency. Specifically, the ultrasound transducers may be selected such that their acoustic frequency responses are non-overlapping. By actuating the transducers in a time interleaved fashion, each sensor may be used to image a surface of a sample at a unique depth. Furthermore, each transducer may be simultaneously actuated with a combination of other transducers to generate higher order harmonics that allow for sub-pixel feature resolution. These principles are depicted by FIGS. 2-3, which shows an example implementation with three ultrasound sensors imaging a subject 300.

Figure 2:
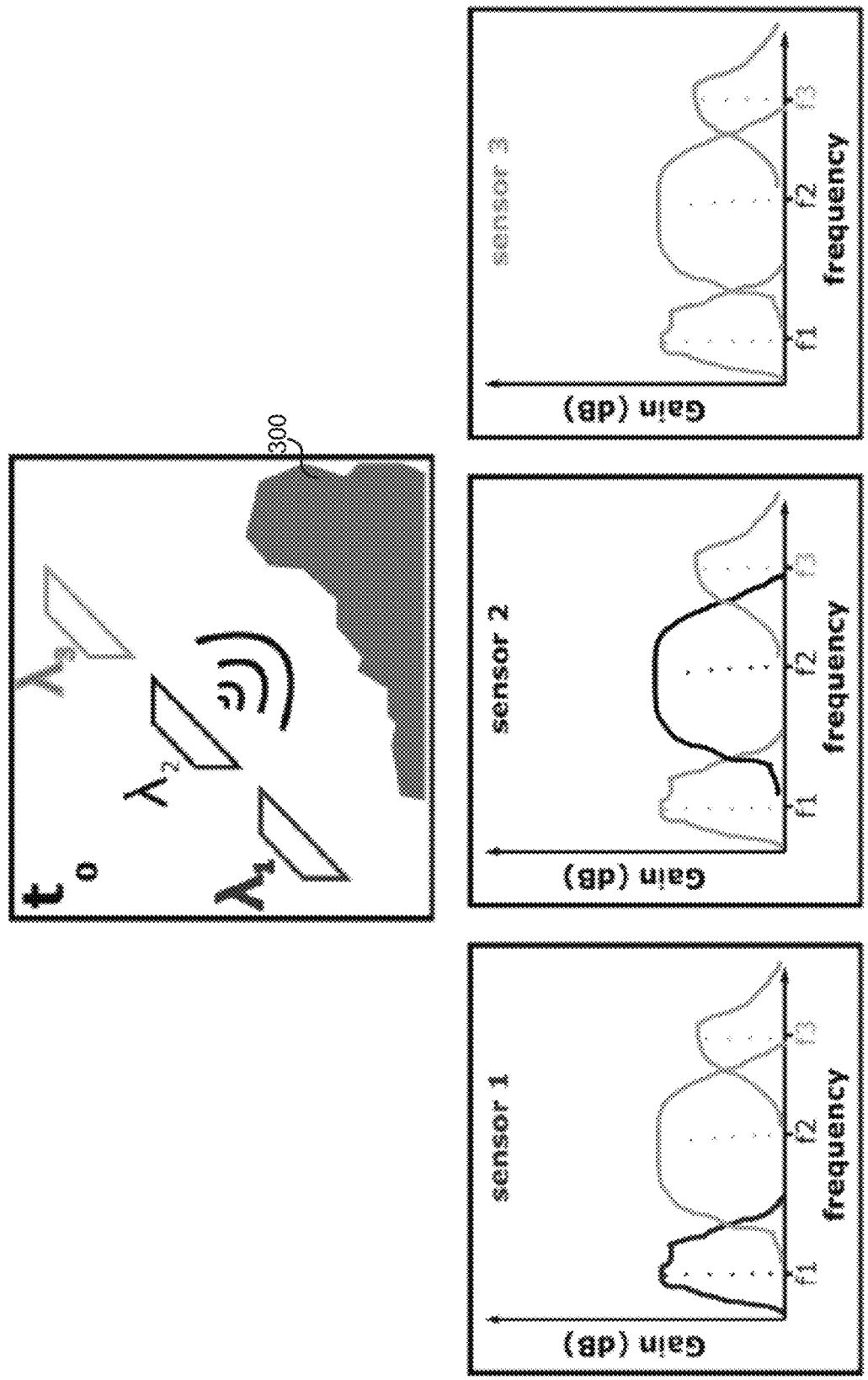
FIG. 2 depicts frequency responses of three ultrasound sensors of a continuous ultrasound measurement device, in accordance with implementations of the disclosure.

As shown by FIG. 2, selecting transducers that are partially overlapping can allow for self-normalization and cross-correlation of signals. In particular, by selecting sensor transducers that are adjacent and partially overlapping in frequency response, the measurement of any pair of sensors may be normalized, thereby reducing systemic sources of noise and significantly increasing signal integrity. Additionally, the simultaneous interrogation of a surface with transducers with distinct resonance frequencies can be used to generate super-resolution ultrasound images. In implementations, the frequency overlap between sensors may be configured to be about 200 KHz or less. In implementations, the frequency overlap between sensors may be configured such that a frequency response range of one sensor does not overlap with a resonant frequency of another sensor. For example, as depicted by FIG. 2, sensor 1 (resonant frequency f1) and sensor 2 (resonant frequency f2) partially overlap in frequency response. Additionally, sensor 2 and sensor 3 (resonant frequency f3) partially overlap in frequency response.

Figure 3:
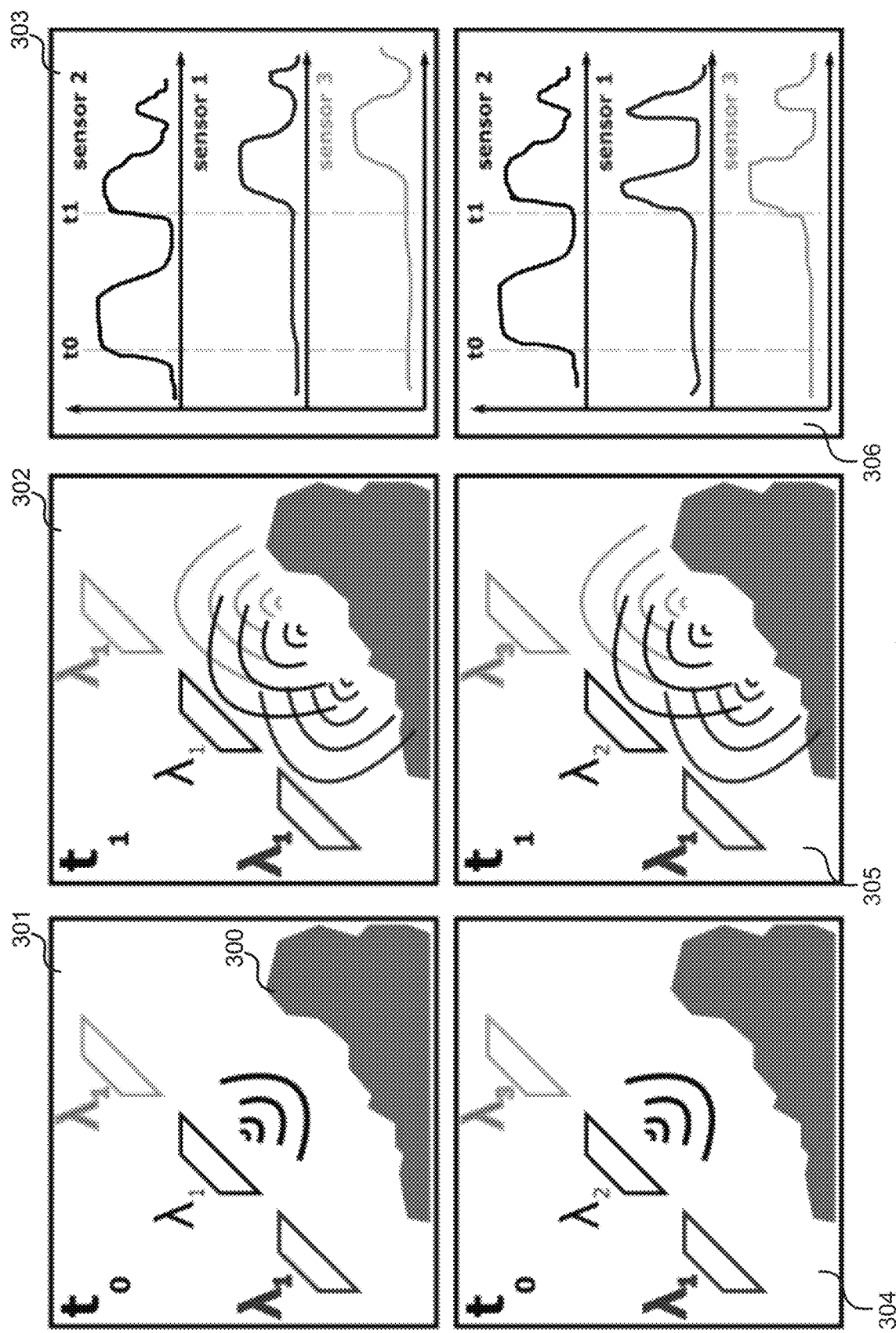
FIG. 3 depicts a technique for cross-correlation in an ultrasound measurement device, in accordance with implementations of the disclosure.

FIG. 3 depicts a technique for cross-correlation in an ultrasound measurement device 100. As depicted, the cross-correlation of signals from any pair of sensors whose frequency responses overlap allows for a redundant measurement of a voxel. Specifically, the transducers of the three sensors may actuated in a time-interleaved fashion. For each actuation (e.g., frame 301), the received echo may be measured by all three transducers (frame 302) to obtain received signals on all three transducers (frame 303). By looking at the correlation of the received signals on all sensors, the signals may be normalized. Frame 303 illustrates the event where the echo from sensor 2's actuation is measured by all three sensors. In this instance, the frequency response of sensors 1 and 3 is convolved in the frequency domain with the received echo waveform. When deconvolved, the measurement from sensor 3 may be correlated with the measurement from sensor 2 while using the measurement of sensor 1 to normalize the measurement of sensor 2. As depicted by frame 306, a much sharper peak in signal monitored by sensor 1 is seen, and those sharper peaks may be achieved by the aforementioned cross-frequency normalization.

Referring again to FIG. 1, processing device 120 may be configured to control operation of the components of device 100, including ultrasound sensors 110 and non-ultrasound sensor(s) 150 (further discussed below). For example, processing device 120 may be configured to cause ultrasound sensors 110 and/or non-ultrasound sensor(s) 150 to perform image acquisition. Additionally, processing device 120 may receive, store (e.g., in machine readable medium 130), and/or process signal measurements received from ultrasound sensors 110 and/or non-ultrasound sensors 150. In some implementations, processing device 120 may also be configured to use signal measurements received from ultrasound sensors 110 to apply the normalization and cross-correlation methods discussed above. The aforementioned methods may be applied in accordance with instructions stored on a machine readable medium 130. In one embodiment, processing device 120 may be implemented as a single integrated circuit (IC) microcontroller that includes memory (e.g., machine readable medium 130) for storing program information and data.

In the example, of FIG. 1, continuous ultrasound measurement device 100 includes a wireless transmitter 140 (e.g., transceiver) that is configured to communicate ultrasound measurement data to wireless receiver 240 (e.g., transceiver) of display system 200. Depending on the ultrasound imaging application, the received ultrasound measurement data may be processed using processing device 210 (e.g., into a format appropriate for display) and/or displayed using display 220. For example, as further discussed below with respect to some implementations, the display 220 may be a component of a cardiac monitor, a mobile device, or some other suitable display device.

The wireless communication link between wireless transmitter 140 and wireless receiver 240 may be a radio frequency link such as a Bluetooth® or Bluetooth® low energy (LE) link, a Wi-Fi® link, a ZigBee link, or some other suitable wireless communication link. In other implementations, data transfer between device 100 and display system 200 may be achieved using a wired transmitter or other suitable wired interface. For example, data may be transferred using a USB-C connector, a USB 2.x or 3.x connector, a micro-USB connector, a THUNDERBOLT connector, an Ethernet cable, etc.

In alternative implementations, display 220 and the functions of display system 200 may be integrated into continuous ultrasound measurement device 100.

Blood Pressure Measurement

In some implementations, continuous ultrasound measurement device 100 may be used in an application for blood pressure measurement. Blood pressure is a critical measurement in patient care. During office visits, it is usually the first vital sign measured. During critical resuscitations in the emergency department, it is usually the primary vital sign used to determine quality of resuscitation, along with heart rate. These measurements in combination are indicators of shock, dehydration, hemorrhage, and provide one of the only quantitative methods of assessing the fluid resuscitation quality in patients requiring fluids. It is also a measure of whether a patient is in cardiopulmonary arrest or has loss of circulation or ventilation.

While these measurements are critical for determining chronic states of health as well as critical for measurements during code situations, presents methods of blood pressure measurement remain as cumbersome and bulky as when it was first developed. Currently, blood pressure is typically measured using a stethoscope and sphygmomanometer. The sphygmomanometer cuff is inflated above the patient's systolic blood pressure to completely occlude the vessel, usually the brachial artery. The air in the sphygmomanometer cuff is then deflated, and the stethoscope is used to listen for the first sounds of turbulent flow after the vessel opens due to reduced pressure. That first sound is then recorded as the systolic pressure as the sound correlates to a cuff pressure.

The sounds of turbulent flow continue until the vessel is completely opened as the cuff is continuously deflated, leading eventually to completely linear flow when the vessel is completely opened. At this time, the loss of the turbulent blood flow, causes the Korotkov sounds (turbulent flow) to cease, and the pressure at which the sounds cease, is recorded as the patient's diastolic blood pressure. The systolic and diastolic pressures then are recorded as the patient's blood pressure. While this is the present "gold standard" for blood pressure measurement, it requires multiple pieces of equipment, and takes several minutes to configure equipment and take a measurement. In a cardiopulmonary arrest situation, where the blood pressure is critical in determining the patient's vital status, these minutes may be invaluable.

Additionally, blood pressure is dynamic and changes on a beat to beat and second by second basis. The conventional method of blood pressure measurement, described above, may not be capable of determining second to second measurement of blood pressure variation, unless invasive measurements are taken using an intraarterial catheter, which is a time consuming and painful endeavor for the patient. The gold standard of blood pressure measurement may also be prone to error from variation in patient anatomy, arm size, cuff size, and the ambient noise in the room.

Figure 4:
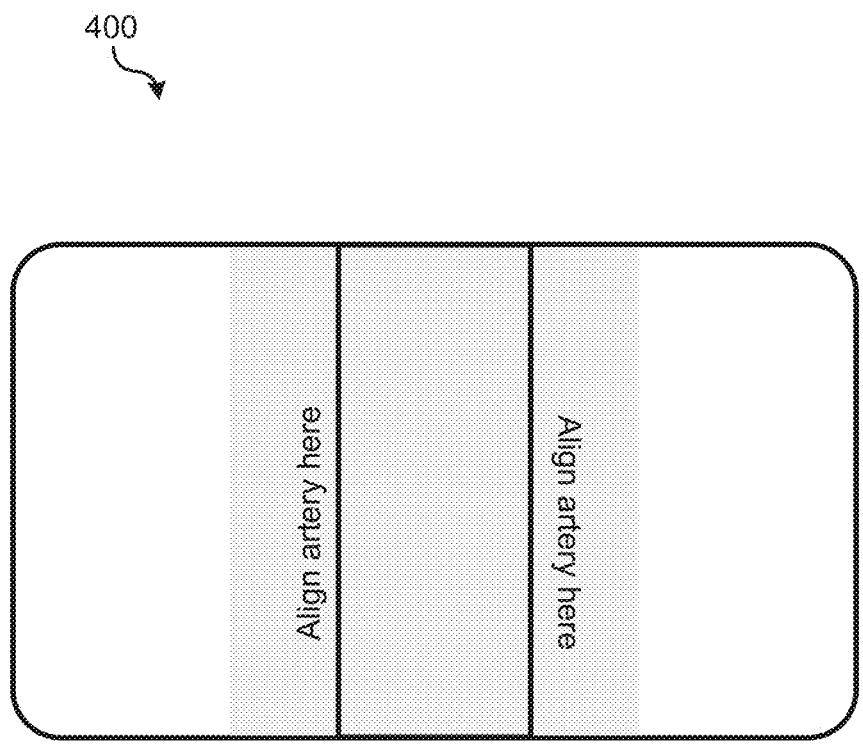
FIG. 4 illustrates one such example implementation of an adhesive substrate including an integrated continuous ultrasound measurement device for monitoring vital signs, including blood pressure, in accordance with implementations of the disclosure.

To address the aforementioned deficiencies of present techniques for blood pressure measurement, continuous ultrasound measurement device 100 may be utilized. FIG. 4 illustrates one such example implementation of an adhesive substrate 400 including an integrated continuous ultrasound measurement device 100 for monitoring vital signs, including blood pressure, in accordance with implementations of the disclosure. As illustrated, substrate 400 includes one or more alignment lines or other markings for aligning ultrasound sensors 110 of an integrated device 100 with an artery of a patient prior to taking ultrasound measurements. Additionally, substrate 400 includes an adhesive (e.g., a rubber, acrylic, or acrylic blend adhesive) on the back that may be used to hold substrate in place and in alignment with the patient's artery. During application, the adhesive may be exposed by peeling away a paper backing. For example, the device can be placed on the patient's neck to measure blood flow velocity and arterial dilation, and thus, blood pressure through the carotid artery. Similar measurements may be made on the radial or ulnar arteries. By virtue of this implementation, the measurement of blood pressure may be noninvasive, reliable, fast, and provide continuous measurement, thus taking into account beat to beat variation. As further discussed below, these continuous variations may be presented to a user on a display system.

Figure 5:
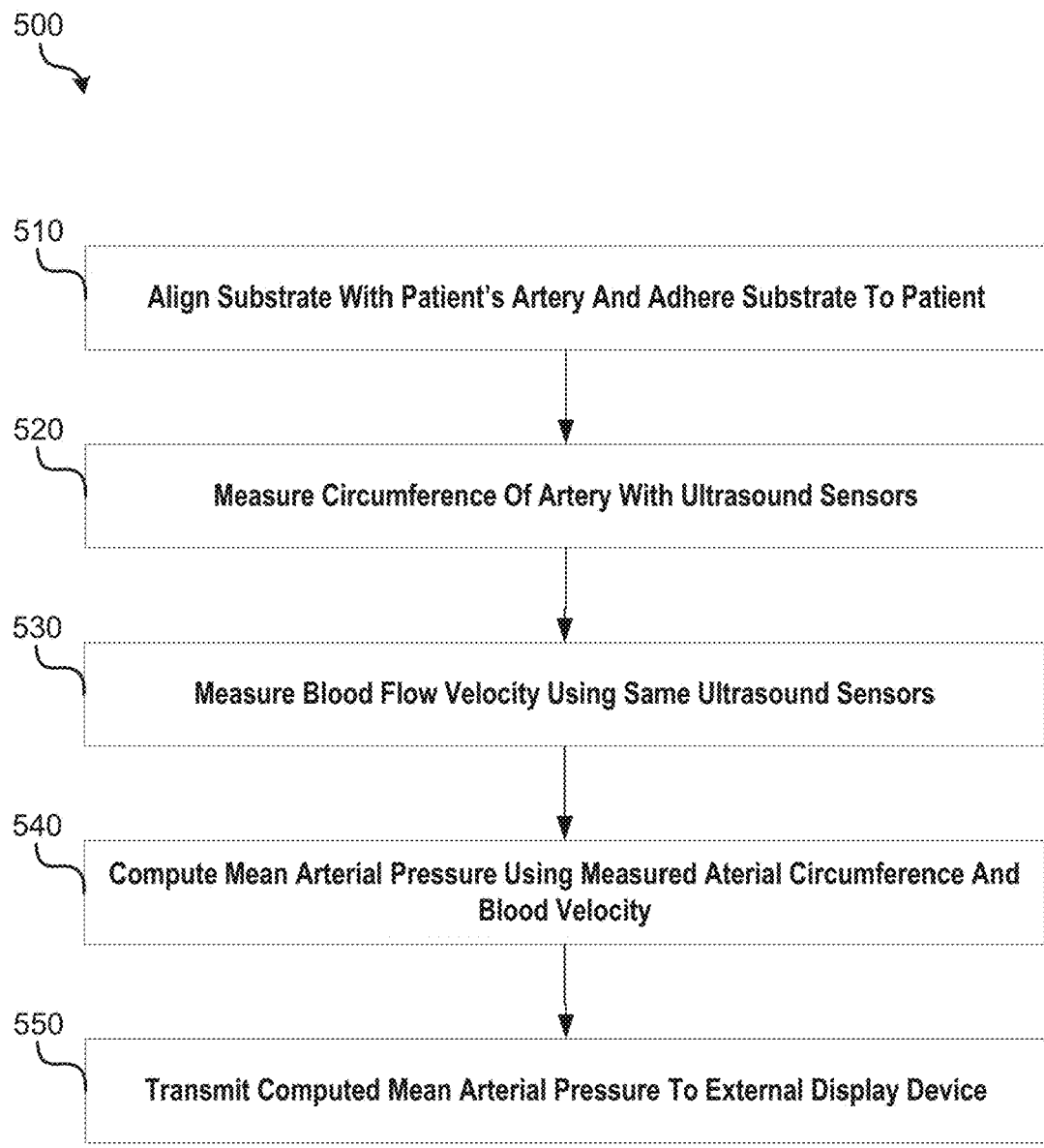
FIG. 5 is an operational flow diagram illustrating an example method for measuring mean arterial pressure using a substrate including a continuous ultrasound measurement device, in accordance with implementations of the disclosure.

FIG. 5 is an operational flow diagram illustrating an example method 500 for measuring mean arterial pressure using a substrate 400 including a continuous ultrasound measurement device 100, in accordance with implementations of the disclosure. At operation 510, the substrate may be aligned with the patient's artery and adhered to the patient using the adhesive. For example, the substrate 400 may be aligned with the patient's carotid artery and subsequently adhered. It should be noted that by virtue of having ultrasound sensors 110 having partially overlapping frequency responses as described herein, the alignment requirements of substrate 400 may be slightly relaxed.

After alignment and placement, at operation 520, the circumference of the artery may be measured with a plurality of ultrasound sensors 110. For example, the circumference may be measured using echo-mode ultrasonography. At operation 530, the patient's blood velocity may be separately monitored using the same ultrasound sensors 110. For example, continuous-wave ultrasound may be utilized to monitor the patient's blood velocity. At operation 540, the patient's mean arterial pressure may be computed using the measured arterial circumference and blood velocity. For example, the patient's mean arterial pressure may be computed by modeling the measured blood velocity as a Stokes flow velocity, and normalizing it by the arterial circumference. In various implementations, a processing device 120 of continuous ultrasound measurement device 100 may perform the necessary DSP and calculations to arrive at the patient's mean arterial pressure.

At operation 550, the computed mean arterial pressure may be transmitted to an external display system 200 (e.g., using a wireless transmitter 140) for display by display 220. In some implementations, device 100 or external display system 200 may also compute and record the patient's respiration and heart rate for display by display 220. The display 220 may be variable based off of the clinician's current display capability. The display 220 may also have the capability of being connected to a portable mobile device, or a cardiac monitor in a hospital setting.

Figure 6A:
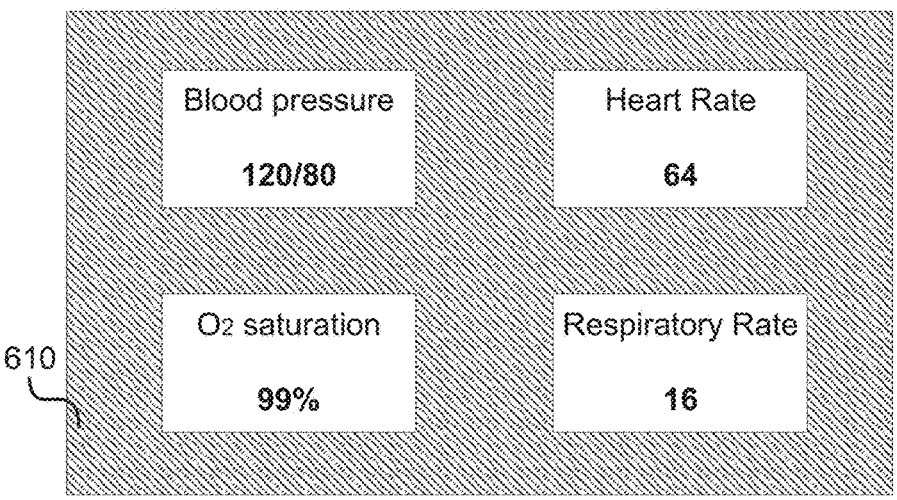
FIG. 6A depicts an example interface that may be presented on a display, as part of patient vital measurements, in accordance with implementations of the disclosure.
Figure 6B:
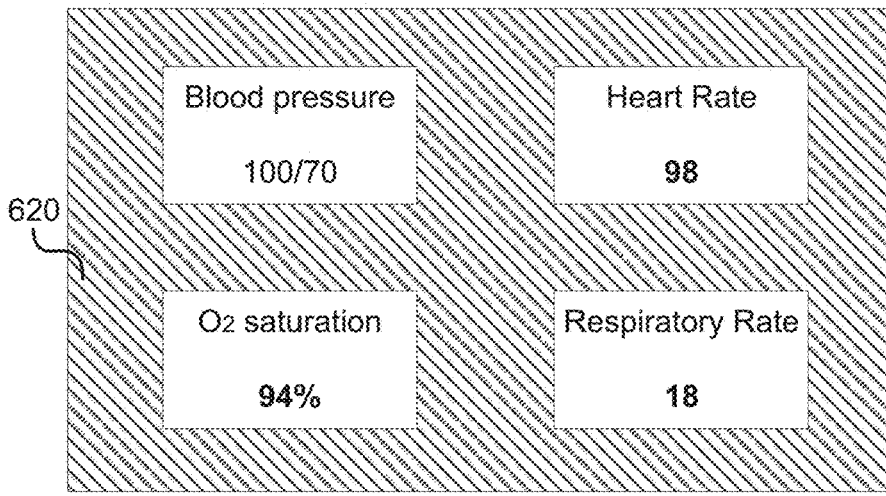
FIG. 6B depicts an example interface that may be presented on a display, as part of patient vital measurements, in accordance with implementations of the disclosure.
Figure 6C:
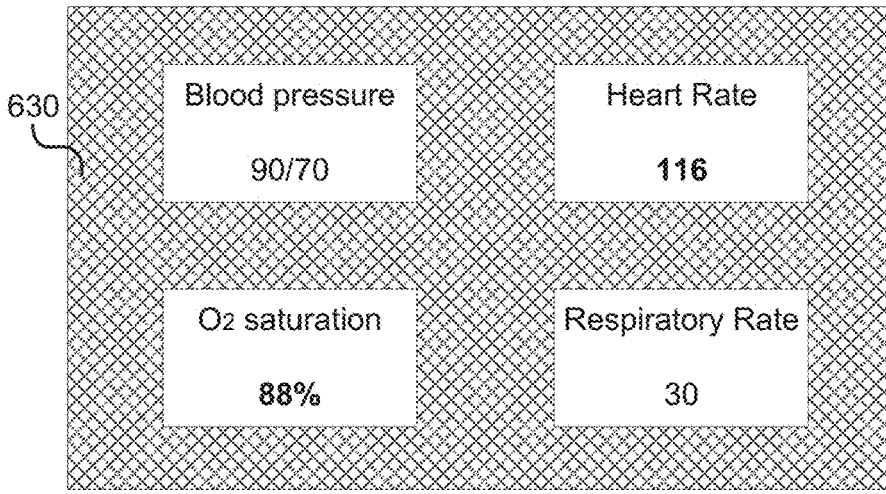
FIG. 6C depicts an example interface that may be presented on a display, as part of patient vital measurements, in accordance with implementations of the disclosure.

FIGS. 6A-6C depict an example interface that may be presented on a display 220, as part of patient vital measurements, in accordance with implementations of the disclosure. For example, the interface may be presented and dynamically updated in real-time by iteratively performing operations 520-550 of method 500. As depicted in this example, blood pressure, heart rate, respiratory rate, and oxygen saturation may be shown on the display 220. The background may change color or otherwise change appearance based on whether or not the values are normal or abnormal. For instance, as depicted by FIG. 6A, when all the values of the vital signs are within normal limits, the background may display a first pattern or color 610 (e.g., green). As depicted by FIG. 6B, when one of the values of the vital signs is intermediately abnormal, the background may display a second pattern or color 620 (e.g., yellow). As depicted by FIG. 6C, when one or more values of the vital signs are grossly abnormal, the background may display a third pattern or color 630 (e.g., red). In contrast with conventional techniques for presenting vitals information (e.g., pulse oximeter showing waveform), the image-based display of the present disclosure may provide an intuitive and silent notification method for tracking vitals.

Referring again to continuous ultrasound measurement device 100, in some implementations, device 100 may include one or more non-ultrasound sensors 150 in addition to the multi-wavelength ultrasound sensors to allow for multi-modal measurement. For example, LED light sources and photodiode receivers may be integrated onto the wireless platform to measure blood oxygenation through pulse oximetry. By way of particular example, a 617 nm LED light source and 583 nm LED light source may be integrated in the device 100. By computing the light absorption ratio in the 583 nm band to the 617 nm band, a metric strongly correlated with blood oxygenation may be obtained. The incident light is differently absorbed by hemoglobin, depending on its oxidative state. An absorption shift from a baseline signal, allows for the measurement of changes in blood oxygenation. Other example sensors that may be implemented include sensors for detecting body fluid status, ejection fraction of the heart, or other vital measurements may be integrated into the hardware/sensor package.

In some implementations, the measurements made using non-ultrasound sensors 150 may be correlated and normalized with ultrasound measurements (e.g., measurements of blood velocity). By virtue of using additional modalities besides ultrasound sensors 110 to measure a characteristic of imaged physiology (e.g., blood velocity), the accuracy of device 100 may be improved.

Figure 7:
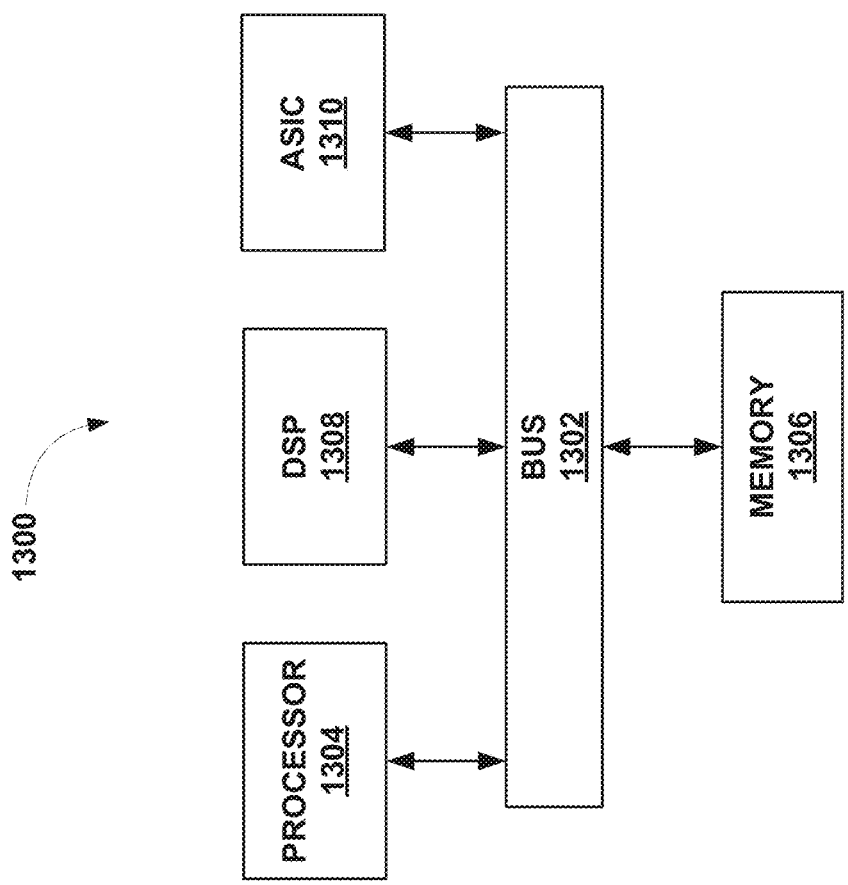
FIG. 7 illustrates an example chip set that can be utilized in implementing architectures and methods in accordance with various implementations of the disclosure.

FIG. 7 illustrates a chip set 1300 in which embodiments of the disclosure may be implemented. Chip set 1300 can include, for instance, processor and memory components incorporated in one or more physical packages. By way of example, a physical package includes an arrangement of one or more materials, components, and/or wires on a structural assembly (e.g., a baseboard) to provide one or more characteristics such as physical strength, conservation of size, and/or limitation of electrical interaction.

In one embodiment, chip set 1300 includes a communication mechanism such as a bus 1302 for passing information among the components of the chip set 1300. A processor 1304 has connectivity to bus 1302 to execute instructions and process information stored in a memory 1306. Processor 1304 includes one or more processing cores with each core configured to perform independently. A multi-core processor enables multiprocessing within a single physical package. Examples of a multi-core processor include two, four, eight, or greater numbers of processing cores. Alternatively or in addition, processor 1304 includes one or more microprocessors configured in tandem via bus 1302 to enable independent execution of instructions, pipelining, and multithreading. Processor 1304 may also be accompanied with one or more specialized components to perform certain processing functions and tasks such as one or more digital signal processors (DSP) 1308, and/or one or more application-specific integrated circuits (ASIC) 1310. DSP 1308 can typically be configured to process real-world signals (e.g., sound) in real time independently of processor 1304. Similarly, ASIC 1310 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

Processor 1304 and accompanying components have connectivity to the memory 1306 via bus 1302. Memory 1306 includes both dynamic memory (e.g., RAM) and static memory (e.g., ROM) for storing executable instructions that, when executed by processor 1304, DSP 1308, and/or ASIC 1310, perform the process of example embodiments as described herein. Memory 1306 also stores the data associated with or generated by the execution of the process.

In this document, the terms "machine readable medium," "computer readable medium," and similar terms are used to generally refer to non-transitory mediums, volatile or non-volatile, that store data and/or instructions that cause a machine to operate in a specific fashion. Common forms of machine readable media include, for example, a hard disk, solid state drive, magnetic tape, or any other magnetic data storage medium, an optical disc or any other optical data storage medium, any physical medium with patterns of holes, a RAM, a PROM, EPROM, a FLASH-EPROM, NVRAM, any other memory chip or cartridge, and networked versions of the same.

These and other various forms of computer readable media may be involved in carrying one or more sequences of one or more instructions to a processing device for execution. Such instructions embodied on the medium, are generally referred to as "instructions" or "code." Instructions may be grouped in the form of computer programs or other groupings. When executed, such instructions may enable a processing device to perform features or functions of the present application as discussed herein.

In this document, a "processing device" may be implemented as a single processor that performs processing operations or a combination of specialized and/or general-purpose processors that perform processing operations. A processing device may include a CPU, GPU, APU, DSP, FPGA, ASIC, SOC, and/or other processing circuitry.

The various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

Each of the processes, methods, and algorithms described in the preceding sections may be embodied in, and fully or partially automated by, code components executed by one or more computer systems or computer processors comprising computer hardware. The processes and algorithms may be implemented partially or wholly in application-specific circuitry. The various features and processes described above may be used independently of one another, or may be combined in various ways. Different combinations and sub-combinations are intended to fall within the scope of this disclosure, and certain method or process blocks may be omitted in some implementations. Additionally, unless the context dictates otherwise, the methods and processes described herein are also not limited to any particular sequence, and the blocks or states relating thereto can be performed in other sequences that are appropriate, or may be performed in parallel, or in some other manner. Blocks or states may be added to or removed from the disclosed example embodiments. The performance of certain of the operations or processes may be distributed among computer systems or computers processors, not only residing within a single machine, but deployed across a number of machines.

As used herein, the term "or" may be construed in either an inclusive or exclusive sense. Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain embodiments include, while other embodiments do not include, certain features, elements and/or steps.

Terms and phrases used in this document, and variations thereof, unless otherwise expressly stated, should be construed as open ended as opposed to limiting. Adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. The presence of broadening words and phrases such as "one or more," "at least," "but not limited to" or other like phrases in some instances shall not be read to mean that the narrower case is intended or required in instances where such broadening phrases may be absent.

What is claimed is:

1. An ultrasound measurement device, comprising:
a processing device; and
a plurality of ultrasound sensors configured to capture tomographic information of a physiological structure, the plurality of ultrasound sensors comprising a first ultrasound sensor including a first transducer having a first frequency response with a first resonant frequency, and a second ultrasound sensor including a second transducer having a second frequency response with a second resonant frequency different from the first resonant frequency, wherein:
the first frequency response partially overlaps with the second frequency response;
the second transducer is configured to transmit an ultrasound signal that is reflected by the physiological structure to create a reflected ultrasound signal;
the first transducer is configured to generate a first received signal from the reflected ultrasound signal;
the second transducer is configured to generate a second received signal from the reflected ultrasound signal; and
the processing device is configured to normalize the first received signal with the second received signal or the second received signal with the first received signal.

2. The ultrasound measurement device of claim 1, wherein the first frequency response does not include the second resonant frequency, and the second frequency response does not include the first resonant frequency.

3. The ultrasound measurement device of claim 1, wherein:
the plurality of ultrasound sensors further comprise a third ultrasound sensor including a third transducer having a third frequency response with a third resonant frequency different from the first resonant frequency and the second resonant frequency;
the third frequency response partially overlaps with the second frequency response but not the first frequency response; and
the third transducer is configured to generate a third received signal from the reflected ultrasound signal.

4. The ultrasound measurement device of claim 3, wherein the processing device is further configured to: correlate the third received signal with the second received signal.

5. The ultrasound measurement device of claim 3, wherein: the third frequency response does not include the second resonant frequency, and the second frequency response does not include the third resonant frequency.

6. The ultrasound measurement device of claim 1, wherein during capture of the tomographic information of the physiological structure, the first transducer and the second transducer are configured to be actuated in a time-interleaved fashion to capture images of a surface of the physiological structure at a plurality of depths.

7. The ultrasound measurement device of claim 1, wherein:
the physiological structure comprises an artery; and
the processing device is further configured to use the plurality of ultrasound sensors to compute a mean arterial pressure through the artery.

8. The ultrasound measurement device of claim 7, wherein the processing device is configured to use the plurality of ultrasound sensors to compute the mean arterial pressure through the artery by performing operations comprising:
measuring, using the plurality of ultrasound sensors, a circumference of the artery,
measuring, using the plurality of ultrasound sensors, a blood flow velocity; and
computing, using the circumference of the artery and the blood flow velocity, the mean arterial pressure.

9. The ultrasound measurement device of claim 8, wherein measuring the circumference of the artery comprises: measuring, with the plurality of ultrasound sensors, using echo-mode ultrasonography, the circumference of the artery.

10. The ultrasound measurement device of claim 8, wherein measuring the blood flow velocity comprises: measuring, with the plurality of ultrasound sensors, using continuous-wave ultrasound, the blood flow velocity.

11. The ultrasound measurement device of claim 7, further comprising: a substrate incorporating the plurality of ultrasound sensors, the substrate including an adhesive surface for adhering to skin of a person.

12. The ultrasound measurement device of claim 11, further comprising: a wireless transmitter incorporated in the substrate, the wireless transmitter configured to transmit the mean arterial pressure to a wireless receiver of a display system.

13. The ultrasound measurement device of claim 7, wherein the processing device is configured to use the plurality of ultrasound sensors to iteratively recompute the mean arterial pressure through the artery.

14. The ultrasound measurement device of claim 13, further comprising: a display that dynamically displays the mean arterial pressure as it is iteratively recomputed.

15. The ultrasound measurement device of claim 1, further comprising: a plurality of non-ultrasound sensors, wherein the plurality of non-ultrasound sensors is configured to make measurements that are correlated and normalized with ultrasound measurements made by the plurality of ultrasound sensors.

16. A method, comprising:
capturing, using a plurality of ultrasound sensors of an ultrasound measurement device, tomographic information of a physiological structure, wherein the plurality of ultrasound sensors comprise a first ultrasound sensor including a first transducer having a first frequency response with a first resonant frequency, and a second ultrasound sensor including a second transducer having a second frequency response with a second resonant frequency different from the first resonant frequency, the first frequency response partially overlapping with the second frequency response;
transmitting, using the second transducer, an ultrasound signal that is reflected by the physiological structure to create a reflected ultrasound signal;

generating, using the first transducer, a first received signal from the reflected ultrasound signal;

generating, using the second transducer, a second received signal from the reflected ultrasound signal; and normalizing the first received signal with the second received signal or the second received signal with the first received signal.

17. The method of claim 16, wherein:

the plurality of ultrasound sensors further comprise a third ultrasound sensor including a third transducer;

the third transducer has a third frequency response with a third resonant frequency different from the first resonant frequency and the second resonant frequency;

the third frequency response partially overlaps with the second frequency response but not the first frequency response; and the method further comprises:

generating, using the third transducer, a third received signal from the reflected ultrasound signal; and correlating the third received signal with the second received signal.

18. The method of claim 17, wherein the first frequency response does not include the second resonant frequency, the second frequency response does not include the first resonant frequency or the third resonant frequency, and the third frequency response does not include the second resonant frequency.

19. The method of claim 16, wherein:

the physiological structure comprises an artery of a person;

the ultrasound measurement device is incorporated in a substrate having an adhesive surface; and the method further comprises:

aligning the substrate with the artery, and after aligning the substrate, adhering the adhesive surface of the substrate to the person.

20. The method of claim 19, further comprising:

iteratively recomputing, using the plurality of ultrasound sensors, a mean arterial pressure through the artery; and wirelessly transmitting, using a wireless transmitter incorporated in the substrate, the mean arterial pressure to a wireless receiver of a display system; and dynamically displaying, using the display system, the mean arterial pressure as it is iteratively recomputed.

* * * * *